US006264653B1

United States Patent
Falwell

(10) Patent No.: US 6,264,653 B1
(45) Date of Patent: Jul. 24, 2001

(54) SYSTEM AND METHOD FOR GAUGING THE AMOUNT OF ELECTRODE-TISSUE CONTACT USING PULSED RADIO FREQUENCY ENERGY

(75) Inventor: Gary S. Falwell, Manchester, NH (US)

(73) Assignee: C. R. Band, Inc., Murray Hill, NJ (US)

( * ) Notice: Subject to any disclaimer, the term of this patent is extended or adjusted under 35 U.S.C. 154(b) by 0 days.

(21) Appl. No.: 09/405,246

(22) Filed: Sep. 24, 1999

(51) Int. Cl.[7] .................................................. A61B 18/18
(52) U.S. Cl. ................................ 606/41; 606/34; 606/42; 606/49
(58) Field of Search ............................... 606/32, 34, 41, 606/42, 49, 46, 38; 128/898

(56) References Cited

U.S. PATENT DOCUMENTS

| | | | |
|---|---|---|---|
| 5,759,158 | 6/1998 | Swanson | 600/508 |
| 5,769,880 | 6/1998 | Truckai et al. | 607/101 |
| 5,840,030 | 11/1998 | Ferek-Petric et al. | 600/439 |
| 5,840,031 | 11/1998 | Crowley | 600/440 |
| 5,935,079 * | 8/1999 | Swanson et al. | 600/509 |
| 6,063,078 * | 5/2000 | Wittkampf | 606/41 |
| 6,071,281 * | 6/2000 | Burnside et al. | 606/41 |
| 6,123,702 * | 9/2000 | Swanson et al. | 606/34 |
| 6,183,468 * | 2/2001 | Swanson et al. | 606/40 |

* cited by examiner

*Primary Examiner*—Linda C. M. Dvorak
*Assistant Examiner*—David M. Ruddy
(74) *Attorney, Agent, or Firm*—Darby & Darby

(57) ABSTRACT

The system and methods of the invention gauge the amount or quality of the contact between body tissue and one or more electrodes supported on a catheter. In further aspects, the invention concerns methods for controlling power delivery to particular electrodes on a catheter in response to tissue contact data derived from that electrode or other electrodes during the ablation procedure. The invention monitors and processes information concerning the number of pulses of pulsed radio-frequency energy that are delivered during an ablation procedure. The amount or quality of tissue contact is gauged by comparing the number of pulses delivered to a particular electrode during the interval to either the number of pulses delivered to at least one other electrode of the plural electrodes or data derived during the ablation procedure. The system and method can provide a display of the gauge of tissue contact among the various electrodes and also can automatically control distribution of pulsed RF energy in response to the gauge of tissue contact.

17 Claims, 3 Drawing Sheets

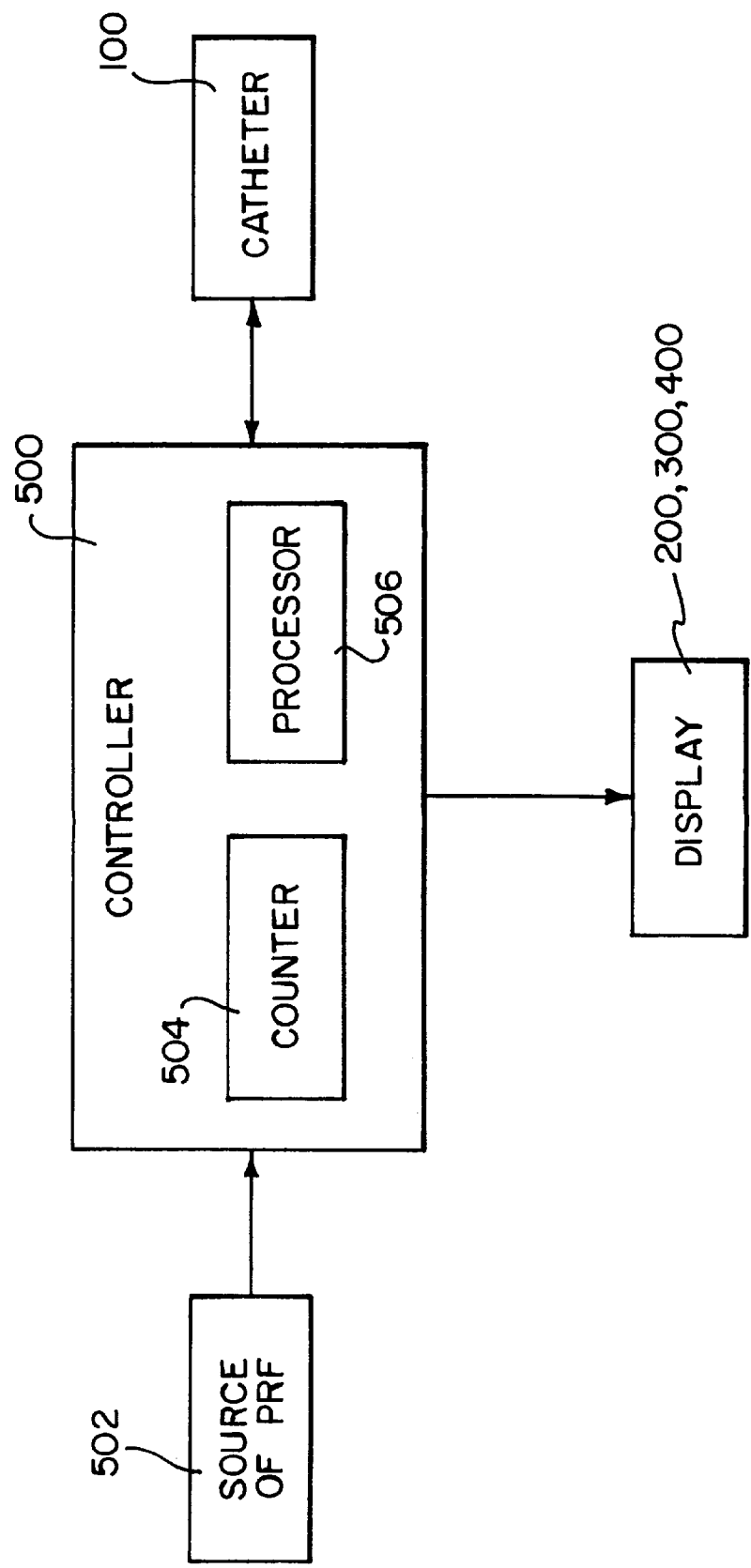

SYSTEM AND METHOD FOR GAUGING THE AMOUNT OF ELECTRODE-TISSUE CONTACT USING PULSED RADIO FREQUENCY ENERGY

FIELD OF THE INVENTION

The present invention relates to improvements in systems for implementing ablation procedures such as cardiac ablation procedures. More particularly, the invention concerns systems for gauging the amount or quality of the contact between body tissue and one or more electrodes supported on a catheter. The invention also concerns methods for controlling power delivery to particular electrodes on a catheter in response to tissue contact data derived from that electrode or other electrodes during the ablation procedure.

BACKGROUND OF THE INVENTION

Standard generators used in catheter ablation procedures provide radio frequency (RF) energy in a unipolar fashion between one or more electrodes supported on an ablation catheter and a ground electrode applied to the patient. The delivery of ablation energy is controlled by monitoring rises in the tissue-electrode interface temperature or tissue impedance.

Recent bench studies comparing a standard generator delivering energy simultaneously to multiple electrodes to delivering pulsed RF (PRF) energy to multiple electrodes shows that pulsing produces contiguous lesions more consistently. Conventional PRF energy delivery systems deliver packets of energy to multiple electrodes at a set frequency. Once an electrode reaches a specified temperature, excess pulsed energy is diverted to a shunt resistor. Studies suggest, however, that the convective heat loss using PRF at the electrode-tissue contact point is faster than the heat conduction within the myocardium. As a result, the peak tissue temperature achieved using PRF energy can occur at depths of approximately 2 mm below the electrode within the myocardium rather than at the electrode-tissue interface. The extent of convective heat loss into the blood pool that circulates about the indwelling ablation catheter will vary with the quality and amount of electrode-tissue contact. When a portion of the ablation electrode surface area is not in contact with tissue ("poor tissue contact"), that portion of the electrode will be exposed to the circulating blood pool, resulting in the temperature sensor on the catheter reading lower temperatures for that electrode than if a greater portion of the electrode were in good contact with the tissue. A conventional system response to the low temperature reading is the application of further PRF energy to that electrode in an attempt to reach and maintain a temperature set point.

In practice, as the temperature at an electrode reaches about 100° C., a sharp impedance rise is detectable as the blood begins to boil and the denatured plasma proteins begin to adhere to that electrode. To counter this occurrence, most generators offer an adjustable impedance cut-off point that will shut down the generator if it detects such an impedance rise (typically, a rise from about 80–100 $\Omega$ to about 150–200 $\Omega$). The risk of having peak tissue temperature reached within the myocardium instead of at the electrode-tissue interface is that super heating of the myocardium can occur and go undetected (i.e., a greater temperature may exist within the body organ than was measured at the electrode/tissue interface). If such a condition is not detected or thwarted, an explosion effect can occur within the myocardium causing extensive tissue damage long before a peak temperature or impedance rise is detected.

What is needed in the art is a system and method for detecting poor tissue contact conditions. What is further needed is such a system and method that can use such data to control pulsed radio frequency energy delivered to a tissue site. The present invention satisfies these and other needs.

SUMMARY OF THE INVENTION

The invention provides methods and a system for monitoring and optionally controlling a catheter ablation procedure.

In one embodiment, the invention provides a method in which a catheter and a pulsed source of RF energy are provided. The catheter can support an arbitrary number of electrodes along its length and at least one temperature sensor. In a preferred embodiment, there are a number of temperature sensors associated with the electrodes, such as one for each electrode. During and throughout an ablation procedure, pulsed radio-frequency energy is provided to the electrodes and the number of pulses delivered to each electrode is monitored over an interval of time. The amount or quality of tissue contact is gauged in this embodiment by comparing the number of pulses delivered to a particular electrode during the interval to either the number of pulses delivered to at least one other electrode of the plural electrodes or data derived during the ablation procedure.

Further preferred features include outputting the comparison to a display, and controlling the number of pulses delivered to any particular electrode in response to the comparison.

In another embodiment, a system for monitoring contact between one or more electrodes and tissue includes a controller coupled between a source of pulsed RF energy and each of several electrodes on an ablation catheter. The controller supplies pulsed RF energy to the electrodes using a gating signal and receives temperature signals throughout the ablation procedure from temperature sensors associated with the electrodes. A counter is provided which registers the number of pulses of RF energy delivered to each electrode. Finally, a processor responds to data gathered by the counter and generates a signal that gauges the amount or quality of tissue contact at each electrode. The processor optionally governs the gating signal automatically to either limit or stop the supply of pulsed RF energy to that electrode based on the contact signals from other electrodes. As a preferred feature, the system provides a continuously updated display of the gauge of tissue contact.

DESCRIPTION OF THE DRAWING FIGURES

FIG. 5 illustrates a system in accordance with the invention.

DETAILED DESCRIPTION

By way of overview and introduction, the present invention provides a system and method for determining the amount or quality of tissue contact at individual electrodes on an ablation catheter by monitoring the relative distribution of pulses to the electrodes during and throughout an ablation procedure. This better ensures that the expected result of a treatment will be obtained. The invention further provides a control system and method responsive to the amount or quality of tissue contact of one electrode as compared to other electrodes or data derived from the ablation procedure to control the power delivery to that electrode.

Figure 1:
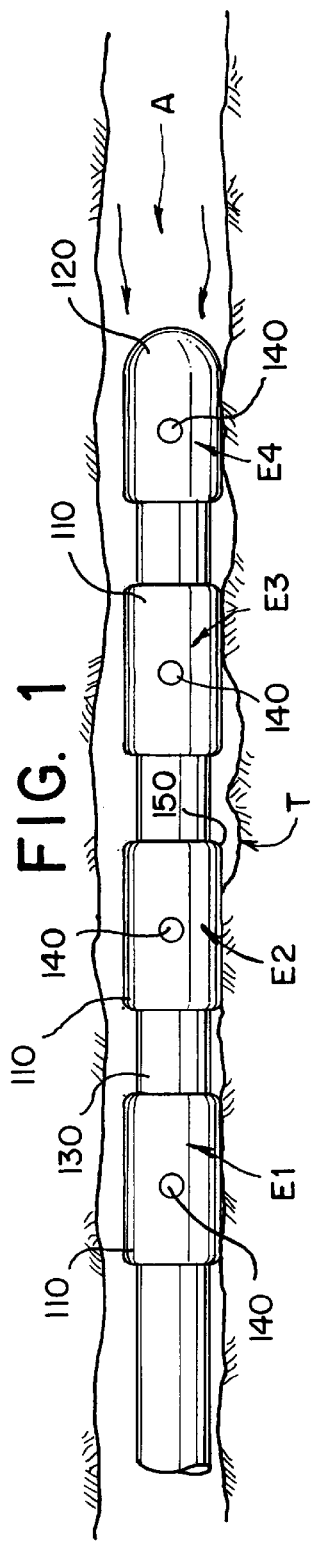
FIG. 1 illustrates a multi-electrode ablation catheter within a body cavity.

With reference now to FIG. 1, a distal portion of a multi-electrode ablation catheter 100 is illustrated. The catheter 100 is designed for creating long continuous lesions at targeted anatomical sites. The ablation catheter includes a plurality of electrodes including ring electrodes 110 and a tip electrode 120 (e.g., 4) supported on a shaft 130. For a description of a suitable multi-electrode catheter, see co-pending U.S. patent application Ser. No. 09/183,728 for RING ELECTRODE STRUCTURE FOR DIAGNOSTIC AND ABLATION CATHETERS, filed Oct. 30, 1998 and assigned to the present assignee, the disclosure of which is hereby incorporated by reference as if set forth in its entirety herein.

The electrodes receive pulsed RF energy from a control unit (e.g., HF Control 2000, AD Elektronik, Wetzlar, Germany) or RF source (neither shown). The pulses are preferably delivered sequentially to the electrodes at a set frequency, but may be delivered simultaneously. The control unit or RF source that delivers PRF energy should be able to deliver pulses to plural electrodes so as to maintain a temperature set point at each electrode. Each electrode preferably has an associated temperature sensor 140, such as a thermistor, thermocouple or the like, which provides a temperature feedback signal to the control unit. Once the set point is reached, the pulses of RF energy can be distributed to a shunt or load resistor, as described in co-pending U.S. patent application Ser. No. 09/091,120 for A DEVICE FOR THE LINEAR HIGH-FREQUENCY CATHETER ABLATION OF ENDOMYOCARDIAL TISSUE, filed Jul. 17, 1998 and assigned to Bard-Angiomed A.G, the disclosure of which is hereby incorporated by reference as if set forth in its entirety herein. Alternatively, the PRF can be distributed to a next electrode 110, 120 in a sequence. However, if the temperature at an electrode that is having its pulses diverted again drops below to the temperature set point, the control unit will cease diverting the energy and instead provide the PRF energy to that electrode.

FIG. 1 illustrates the catheter tip 10 positioned within a body passageway such as an artery having blood circulating in the direction of arrow A. Were all of the electrodes 110, 120 in good tissue contact, they would cool relatively uniformly and receive equal amounts of PRF energy to maintain a desired temperature set point. However, typically there is at least one electrode that is not making as good tissue contact as the other electrodes and is instead being cooled by the circulating blood in the body passageway. The cooling effect of the blood pool reduces the temperature sensed at that electrode, causing the controller to send additional pulses to that electrode in an attempt to achieve the set point temperature. Because the electrodes are endoluminally positioned, the operator cannot directly visualize the quality or amount of contact with tissue, leaving the operator to rely on measured data such as impedance and temperature data.

With further reference to FIG. 1, the three ring electrodes 110 and the tip electrode 120 are labeled E1, E2, E3 and E4, respectively. Each of these electrodes makes varying degrees of contact with the tissue T of the body passageway. As can be appreciated from the drawing, electrodes E1 and E4 have similar contact area with tissue T, electrode E2 is mostly in contact with tissue T (save for its distal end 150), and electrode E3 makes poor contact with tissue T with more of its surface exposed to the circulating blood than the other electrodes on the catheter 10. Consequently electrode E3 will be cooled more rapidly by the blood pool as compared to the other electrodes which have made better tissue contact.

The traditional approach of using temperature measurements to control the ablation procedure and prevent tissue overheating would distribute a greater number of pulses of RF energy to electrode E3 in an attempt to raise its temperature to the temperature set point. That circumstance can lead to undesirable heating effects such as super heating of the myocardium described above. In accordance with the invention, however, the operator is provided with information that electrode E3 is not in good tissue contact and that it, in fact, requires (1) fewer pulses to avoid unwanted physiological effects or (2) repositioning to improve its contact. The operator can make necessary adjustments in view of this information, or the system can respond automatically by controlling the number of pulses delivered to any electrode that is in poor tissue contact.

Surprisingly, by monitoring the pulse distribution at each electrode the degree of tissue contact can be gauged. For example, if an electrode such as electrode E3 is not in good contact with tissue and is instead being cooled by the blood pool, a greater amount of pulses will be distributed to that electrode as compared to electrodes E1, E2 and E4. If a single electrode requires a greater amount of energy than the remaining electrodes, in one arrangement in accordance with the invention a limit is set to slow or stop energy delivery to that electrode. In addition, a calibration factor may be taken into account when calculating the energy ratio among the various electrodes to account for, among other things, differences in size, shape, and thermal mass of the electrodes 110, 120.

By maintaining the electrodes in good contact with the target tissue, problems associated with excessive electrode temperature in the blood pool are eliminated.

It should be understood that the traditional approach of using impedance measurements is useful to establish tissue contact prior to the procedure, but is ineffective in providing a meaningful measure of tissue contact throughout the procedure, and cannot be used to determine whether the catheter, or one or more electrodes supported thereon, has moved after the procedure has started.

| Row No. | Data | E1 | E2 | E3 | E4 |
|---|---|---|---|---|---|
| 1. | No. of Pulses in a First Interval | 4 | 6 | 10 | 4 |
| 2. | Avg. No. of Pulses In the First Interval Period | 6 | 6 | 6 | 6 |
| 3. | Pulse Ratio wrt Avg. | 0.66 | 1.00 | 1.66 | 0.66 |
| 4. | Gauge of Contact as Inverse of Pulse Ratio | 1.52 | 1.00 | 0.60 | 1.52 |
| 5. | Share of Total Pulses Delivered in the First Interval | 16.66% | 25% | 41.66% | 16.66% |
| 6. | Gauge of Contact Based on Share | 84% | 75% | 58% | 84% |
| 7. | No. of Pulses In a Reference Position at a Reference Interval | 4 | 6 | 5 | 4 |

-continued

| Row No. | Data | E1 | E2 | E3 | E4 |
|---|---|---|---|---|---|
| 8. | No. of Pulses In a Successive Position at a Successive Interval | 10 | 5 | 4 | 5 |
| 9. | Change In Contact | 6 | −1 | −1 | −1 |
| 10. | Change Relative to Reference Position | −50% | +16.6% | +16.6% | −16.6% |

With reference to the Table above, the total pulses delivered to the electrodes E1–E4 in a first interval such as a set time period is twenty four and the average number of pulses to each electrode in that time period is six. The pulse ratio of pulses delivered to each electrode E1–E4 over the interval (Row 3) is computed by dividing the number of pulses delivered to a respective electrode (Row 1) by the average number of pulses (Row 2). This pulse ratio provides a basis for gauging the amount or quality of tissue contact. In particular, if a particular electrode has a pulse ratio less than unity (e.g., E1 and E4 in the Table above), it is receiving fewer pulses in the interval than other electrodes supported on the same catheter which indicates good tissue contact has been established for that electrode because it is maintaining a set point temperature with fewer pulses. On the other hand, if a given electrode has a pulse ratio greater than unity (e.g., E3 in the Table above), it is receiving more pulses in the interval than other electrodes supported on the same catheter which indicates poor tissue contact for that electrode insofar as it requires a comparatively greater number of pulses to maintain the set point temperature. To the extent that a particular electrode has a unity pulse ratio, the quality of tissue contact can only be improved if one of the other electrodes has fewer pulses over the time interval than that electrode or, equivalently, a lower pulse ratio. For example, electrode E2 in the Table above has a unity pulse ratio and its quality of tissue contact can be improved because other electrodes (E1 and E4) have fewer pulses in the same interval (and also a lower pulse ratios). A gauge of the quality or amount of tissue contact of one electrode compared to the others can be expressed, for example, as the inverse of the computed pulse ratio (Row 4). In the Table above, the gauge of tissue contact ranges from 0.60 to 1.52, where higher numbers indicate better tissue contact.

Figure 2:
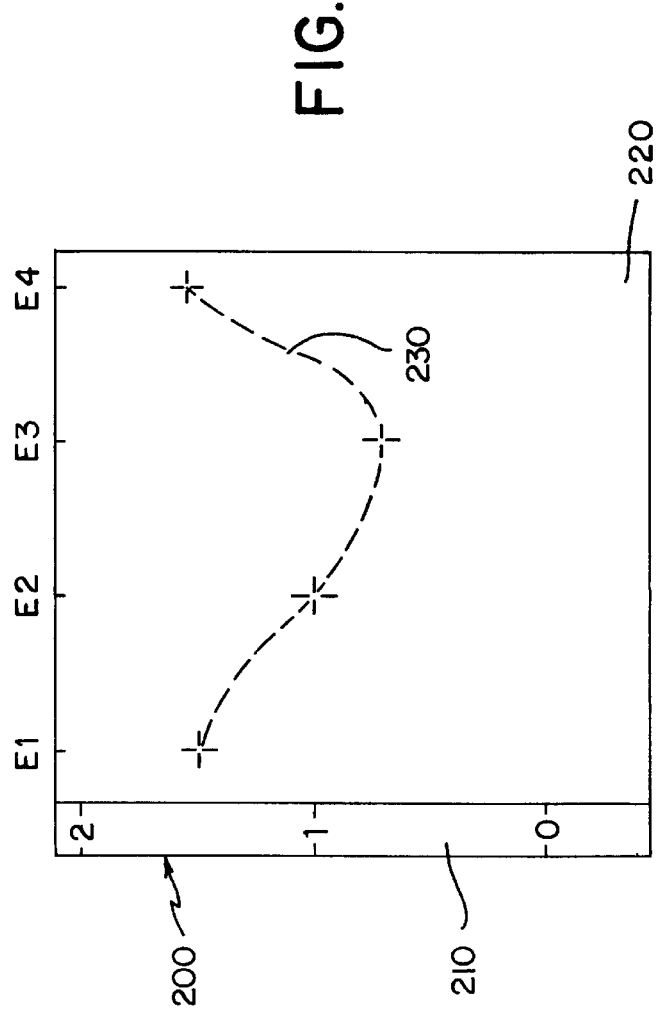
FIG. 2 illustrates the simultaneous display of tissue-contact data for plural electrodes of the multi-electrode catheter of FIG. 1.

In one preferred mode of the invention, the gauge of tissue contact is shown on a display and continuously updated to guide an operator during an ablation procedure. In this mode, the operator is presented with a graphical representation of the relative tissue contact for each electrode, as shown in FIG. 2. Preferably, the graphical representation is provided on a display 200 connected to the RF source or a switching network such as the HF Control 2000, available from AD Elektronik, Wetzlar, Germany. The display 200 preferably is an LCD display unit or a computer monitor, but may comprise any other device capable of displaying changing data including discrete or bar-mounted LEDs. The display of FIG. 2 displays the gauge of tissue contact at a scale appropriate to the data that was empirically gathered during the ablation procedure, such as the data shown in the first four rows of the Table. A scale 210 is established in a conventional marner to clearly display the variations in quality or amount of contact. For example, the scale may have its maximum and minimum values assigned to be the rounded-up and rounded-down values of the maximum and minimum gauge of contact data (Row 4), respectively. For example, the maximum value in the data in Row 4 of the Table is 1.52 which is rounded-up to 2 and the minimum value 0.60 in that row is rounded-down to 0. The data points for each electrode are displayed in a field 220, with each data point from an electrode preferably being positioned within the field 220 in the same order that the electrode is supported on the catheter. Optionally, the data points can be fitted to a curve 230 such as a second- or third-order curve to provide the operator with interpolated data concerning the quality or amount of tissue contact by the electrodes along the catheter.

Within the scope of the present invention are other bases for gauging tissue contact. For example, and with further reference to the Table above, the share of the total number of pulses delivered to each electrode can be computed by dividing the number of pulses delivered to a particular electrode by the total number of pulses delivered to all electrodes over the interval. In the first interval shown in the Table (Row 1), twenty-four pulses were delivered to electrodes E1–E4, and the share of this total that was delivered to a particular electrode ("X") can be expressed as a percentage (Row 5). The quality or amount of tissue contact for each electrode can be gauged from this data, and is expressed as 1-X in Row 6 of the Table. This gauge of contact shows that electrodes E1 and E4 have the same relative degree of tissue contact, which is somewhat better than that of electrode E2 and much better than that of electrode E3.

Figure 3:
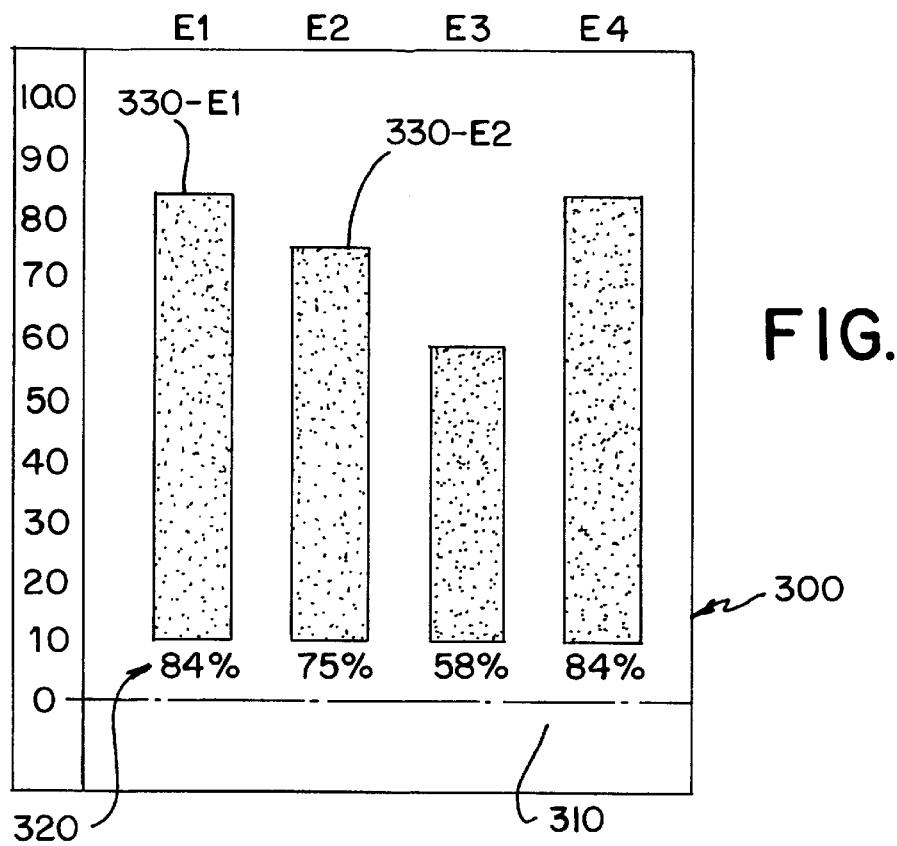
FIG. 3 illustrates a variation of the simultaneous display of tissue-contact data illustrated in FIG. 2.

A display 300 shown in FIG. 3, which may be the same unit as used for the display 200, can be used to display continuously updated tissue-contact data to guide an operator during an ablation procedure. Preferably, the display shows for each electrode supported on the catheter both a numeric and graphic representation of the gauge of tissue contact data from Row 6 in a field 310. For example, electrode E1 was determined as having an 84% gauge of tissue contact based on the comparatively few pulses delivered to that electrode over the interval under consideration. That figure, 84%, is shown at location 320 in the field 310. In addition, a bar is depicted at location 330-E1 which graphically represents the relative degree of tissue contact by to the electrode E1. Alongside bar 330-E1 are bars 330-E2, 330-E3, etc. (more generally, bars 330) for each electrode that is supported on the catheter that is being monitored. Together, the bars 330 comprise a bar graph which provides the operator with a quick comparison of the relative amount or quality of all of the electrodes being monitored, simultaneously.

Figure 4:
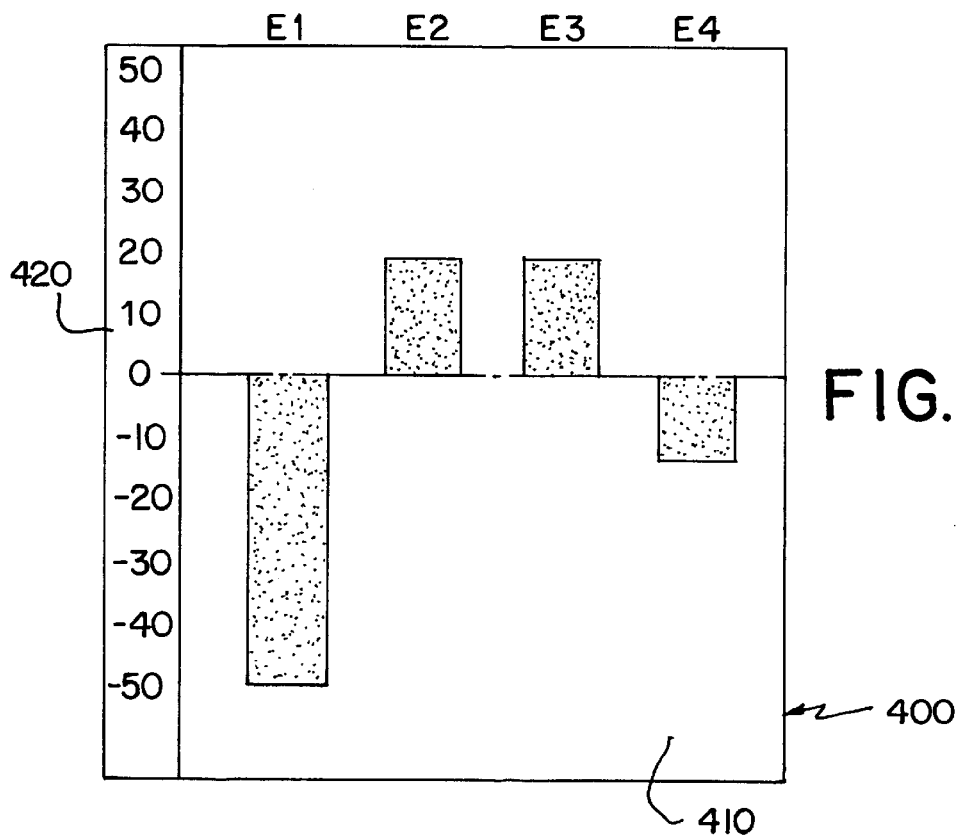
FIG. 4 illustrates a simultaneous display of changes in tissue contact data with changes in position of an indwelling catheter such as the multi-electrode catheter of FIG. 1.

The amount or quality of tissue contact that a given electrode is making can also be gauged relative to data derived during the ablation procedure other than the number of pulses delivered to each electrode. In one alternate mode, the operator may establish a reference position of the indwelling catheter, for example, once he or she has positioned the catheter so that relatively good tissue contact is gauged, as can be illustrated on either of the displays 200, 300. The operator can establish the position of the catheter as the reference position, with the number of pulses being delivered to maintain tissue temperature noted during a reference interval (Row 7). The reference position can be established, for example, using a button or other control (e.g. a button or control on the device housing the display 200,300). The operator can then make slight changes in the catheter position in an effort to further improve tissue contact at one or more of the electrodes. At each successive interval, the number of pulses delivered to each electrode being monitored can be recorded (see Row 8), and the difference can be computed on an electrode-by-electrode basis (see Row 9) in order to determine whether there has been a change in the quality or amount of contact. Such a determination can be inferred directly from an increase or decrease in the number of pulses required to maintain the temperature set point. The percent change in the successive interval verses the reference interval can be determined (Row 10), or some other change calculated, and that change can be displayed in a window or display 400, as shown in FIG. 4. Preferably, an increase in the number of pulses between the reference interval and the successive interval is displayed as a decrease in the amount or quality of the tissue contact (because more energy is required to maintain the temperature set point), and a decrease in the number of pulses between the reference interval and the successive interval is displayed as an increase in the amount or quality of the tissue contact (because less energy is required to maintain the temperature set point). The change in tissue contact relative to the reference position data is displayed in a field 410, in accordance with a scale established in a conventional manner and preferably displayed in a field 420.

As will be understood by those of skill in the art, the amount or quality of tissue contact that a given electrode is making can further be gauged using a reference position and a variety of data measured or derived during the ablation procedure concerning other electrodes supported on the same catheter.

A system in accordance with the invention can be configured to monitor the degree of contact between tissue and one or more electrodes throughout an ablation procedure. As shown in FIG. 5, the system includes a controller 500 connected or coupled between a source of pulsed RF energy 502 and each of several electrodes supported on the catheter 100. The controller supplies pulsed RF energy to each electrodes 110, 120 using a gating signal. The gating signal gates the transmission of pulses from the RF source to each electrode. Preferably, the electrodes are energized serially and the number of pulses that are conveyed to any particular electrode is established by the present gating signal setting for that electrode.

The controller 500 receives temperature signals from temperature sensors associated with each electrode. In addition, the controller governs the settings of the gating signal to increase, decrease, limit or stop the delivery of pulsed RF energy to any particular electrode.

The system in accordance with this aspect of the invention includes a counter 504 which registers the number of pulses of RF energy delivered to each electrode, for example, within the controller 500 as shown. The counter can be implemented as a programmed routine running under control of a processor 506, or can be a circuit component. A processor 506 is also preferably included within the controller 500 and is responsive to data gathered by the counter to generate a signal that gauges the amount or quality of tissue contact at each electrode, in the manner described above. The gauge of tissue contact is preferably provided on a continuously updated display, such as the displays 200, 300, 400.

In one arrangement, the processor automatically and selectively alters the gating signal of each particular electrode in response to data derived during the ablation procedure through its governance of the gating signal. As a result, the gating signal for a particular electrode can be altered to either increase, limit or stop the supply of pulsed RF energy to that electrode based on the contact signals from other electrodes and thereby prevent super heating of the myocardium. In a presently preferred form, however, the operator manually alters the gating signal, for example, after reviewing the data displayed on the display 200, 300, 400.

The methods and system of the present invention can prevent undesired physiological heating effects to the heart such as to the myocardium, as well as other body organs where a suitably sized ablation catheter can be used such as the brain.

The invention has been described in connection with a particular embodiment but is defined without limitation by the claims appended hereto and includes insubstantial variations in elements and method steps.

I claim:

1. A method for monitoring a catheter ablation procedure, comprising the steps of:
    (a) providing a catheter having a plurality of electrodes supported along its length and at least one temperature sensor;
    (b) providing pulsed radio-frequency energy to the plural electrodes from a source of RF energy;
    (c) for each of the plural electrodes, monitoring the number of pulses delivered to that electrode during an interval of time; and
    (d) gauging an amount of tissue contact by comparing the number of pulses delivered to a particular electrode during the interval to the number of pulses delivered to at least one other electrode of the plural electrodes.

2. The method as in claim 1, including the additional step of outputting the result of the comparison.

3. The method as in claim 1, including the additional step of controlling the number of pulses delivered to the particular electrode in response to the comparison.

4. The method as in claim 3, wherein the controlling step comprises:
    i. locating an electrode among the plurality of electrodes which is making comparatively good tissue contact;
    ii. identifying the total number of pulses that were delivered during the interval to the located electrode; and
    iii. decreasing the number of pulses delivered to the particular electrode in the event that the number of pulses delivered to the particular electrode exceeds then number of pulses delivered to the located electrode by a predetermined factor.

5. The method as in claim 4, wherein the predetermined factor is one of a number and a percentage.

6. The method as in claim 5, wherein the predetermined factor is a percentage and wherein the number of pulses delivered to the particular electrode is decreased if the total number of pulses delivered to the particular electrode during the interval exceeds the total number of pulses delivered to the located electrode by about at least 25%.

7. The method as in claim 1, wherein the number of pulses delivered to the particular electrode during the interval is compared to an average number of pulses delivered to all of the plural electrodes.

8. The method as in claim 1, wherein the time interval is the same for each of the plural electrodes.

9. The method as in claim 1, further comprising a tip electrode at the tip of the length of the catheter and wherein the steps of providing pulsed energy and monitoring the number of pulses include providing pulsed energy to the tip electrode and monitoring the number of pulses provided to the tip electrode.

10. The method as in claim 1, wherein each of the plurality of electrodes has an associated temperature sensor.

11. A method for monitoring a catheter ablation procedure, comprising the steps of:
    (a) providing a catheter having a plurality of electrodes supported along its length and at least one temperature sensor;

(b) providing pulsed radio-frequency energy to the plural electrodes from a source of RF energy;

(c) for each of the plural electrodes, monitoring the number of pulses delivered to that electrode during an interval of time; and (d) gauging an amount of tissue contact by comparing the number of pulses delivered to a particular electrode during the interval to data derived during an ablation procedure.

12. A method for monitoring a catheter ablation procedure, comprising the steps of:

(a) providing a catheter having a plurality of electrodes supported along its length and a number of temperature sensors positioned along the catheter to sense the temperature at each of the electrodes;

(b) providing pulsed radio-frequency energy to the plural electrodes from a source of RF energy;

(c) for each of the plural electrodes, monitoring the number of pulses delivered to that electrode during an interval of time; and (d) gauging an amount of tissue contact by comparing the number of pulses delivered to a particular electrode during the interval to data derived during an ablation procedure.

13. The method as in claim 12, where in there is one temperature sensor for each electrode.

14. A system for monitoring contact between one or more electrodes supported on a catheter and tissue within a patient during an ablation procedure in which energy is provided to the electrodes from a source of pulsed RF energy and in which each electrode has an associated temperature sensor, comprising:

(a) a controller coupled between the source of pulsed RF energy and each of the electrodes, the controller supplying pulsed RF energy to the electrodes using a gating signal and receiving temperature signals from the temperature sensors during the ablation procedure;

(b) a counter which registers the number of pulses of RF energy delivered to each electrode;

(c) a processor responsive to data gathered by the counter to generate a contact signal that gauges the amount or quality of tissue contact at each electrode.

15. The system as in claim 14, further comprising a continuously updated display of the gauge of tissue contact.

16. The system as in claim 14, wherein the processor governs the gating signal.

17. The system as in claim 16, wherein the gating signal for a particular electrode is altered to either limit or stop the supply of pulsed RF energy to that electrode based on the contact signals from other electrodes.

* * * * *